United States Patent [19]

Malmros

[11] 4,334,880
[45] Jun. 15, 1982

[54] ANALYTICAL DEVICE HAVING SEMICONDUCTIVE POLYACETYLENE ELEMENT ASSOCIATED WITH ANALYTE-BINDING SUBSTANCE

[76] Inventor: Mark K. Malmros, Box 106, Washington Crossing, Pa. 18977

[21] Appl. No.: 198,782

[22] Filed: Oct. 20, 1980

[51] Int. Cl.³ .................. G01N 27/12; G01N 33/54
[52] U.S. Cl. .................. 23/230 B; 23/915; 324/71 SN; 422/68; 424/12; 435/4; 435/7; 435/291
[58] Field of Search .......... 23/230 B; 424/12; 324/71 SN; 422/68; 435/4, 7, 291

[56] References Cited

U.S. PATENT DOCUMENTS

| | | | |
|---|---|---|---|
| 3,932,807 | 1/1976 | Wilson | 324/71 SN |
| 3,999,122 | 12/1976 | Winstel | 324/71 SN |
| 4,103,227 | 7/1978 | Zemel | 324/71 SN |
| 4,180,771 | 12/1979 | Guckel | 324/71 SN |

OTHER PUBLICATIONS

Jay N. Zemel, Research/Development, 38-44, Apr. 1977.
J. N. Zemel, Anal. Chem., 47(2), 255A-268A, (1975).
P. Bergveld et al., Nature, 273, 438-443, (Jun. 8, 1978).
Heeger and MacDiarmid, "Semiconducting and Metallic Organic Polymers:Chemically Doped Polyacetylene, $(CH)_x$".

Primary Examiner—Sidney Marantz

[57] ABSTRACT

A method, sensor and semiconductor device for determining the concentration of an analyte in a medium. The device features an element constructed of polyacetylene associated with a binding substance having specific affinity for the analyte.

12 Claims, 2 Drawing Figures

ANALYTICAL DEVICE HAVING SEMICONDUCTIVE POLYACETYLENE ELEMENT ASSOCIATED WITH ANALYTE-BINDING SUBSTANCE

BACKGROUND OF THE INVENTION

Immunoassays have been used routinely for the identification and quantitation of haptens, antigens and antibodies (all broadly termed analytes). The basic principle of all immunoassays is predicated on the specific binding between components of a reaction pair (e.g. antigen-/antibody, hapten/antibody, etc.) where, in some cases, one component is labeled in such a fashion as to be easily analyzed by some external means.

Radioimmunoassay (RIA) is based on the use of a radioisotope as a label for one of the components of a specific binding pair. A radioisotopically labeled component can then be detected by counting the radiation emitted by the isotope using a suitable instrument.

Other methods of labeling one component of a specific binding pair have been developed. The use of enzyme and fluorescent labels have recently been employed and are termed enzyme immunoassay (EIA) and fluorescent immunoassay (FIA) respectively. Again, with the use of suitable reagents and instruments, these labels can be used for the determination of analytes in a liquid medium. Many variations to the basic procedures are in use, but most require the steps of reaction, separation, and detection of label.

More recently, electrochemical sensors have been employed in an effort to simplify and/or improve the sensitivity of these procedures. Basically, they employ an ion selective electrode to detect the reaction product of an enzyme which has been used as a label for one component of a specific binding pair.

The present invention seeks to eliminate the preparation of a labeled component of a specific binding pair, the separation of such a component from the assay system, as well as its subsequent detection; thereby greatly simplifying the method of performing an immunoassay. More specifically, the present invention relates to a new and useful improvement in a method for the determination of analytes in a liquid medium by the use of a biochemically sensitive semiconductor device set forth in the following description and specifications.

DESCRIPTION OF THE INVENTION

All numbers in parenthesis refer to elements in FIGS. 1 and 2.

The present invention relates to a device to be used in a method for the determination of analytes in a liquid medium. More specifically, the present invention relates to a device, composed of an electrically semiconductive material (1) to which an analyte specific binding substance (2) is suitably immobilized to said material in such a fashion that the binding of said analyte (3) to its specific binding substance alters the electrical semiconductive properties in a measureable way. Further, the present invention relates to a method of determining the presence of an analyte in a liquid medium using such a device.

As most specific binding substances for any particular analyte are biological in origin, said device is termed a biochemically sensitive semiconductor device or BSSD. These specific binding substances are generally of an organic chemical nature, displaying certain measureable properties of which one is a specific electrical charge. Furthermore, for a specific binding substance, its electrical charge will vary as a result of its binding to its particular analyte; an example of a binding substance and its specific analyte is an antibody and its specific antigen. Examples of specific binding substances are: antibodies, antigens, enzymes, enzyme substrates, enzyme substrate analogs, agglutinins, lectins, enzyme cofactors, enzyme inhibitors and hormones. This invention seeks to detect and measure the binding of an antigen (analyte) by its specific antibody (binding substance) by detecting and measuring the change in the electrical charge of one or both elements of the binding reaction. By placing either one of the two elements of a specific binding system in close proximity to a material which can be influenced by the field of the electrical charge, a change in that electrical field as a result of the binding reaction will effect a change in the properties of that material. If the properties of this material are measureable, it follows that the binding reaction is also measureable.

A class of materials which can be used to satisfy the aforementioned description are known as semiconductors. These materials display electrical characteristics between that of a good electrical conductor, such as copper, and a good electrical insulator, such as glass; hence the term "semiconductor". The properties of a material that provide for its semiconductive characteristics depend on the number of electrons in that material available to move freely through such a material under the influence of an externally applied electric field. All materials are composed of atoms, themselves further comprised of various particles, one of which is termed an electron. An electron is by definition one unit of negative electrical charge. Thus, while all materials are comprised, in part, of electrons, not all electrons are available to move freely through such a material under the influence of an externally applied electric field; these electrons are termed valence electrons and are tightly held to its atom by various nuclear and electrical forces. Those electrons which can move freely through a material, thus conducting electricity, are said to be in a conductive band.

A semiconductive material contains conductive and valence electrons, either naturally or by design. Silicon, for example, can be "doped" with various elements to create either an excess of electrons, or a scarcity of electrons, also termed "holes". Furthermore, such semiconductive materials can exhibit either an increase or a decrease in electrical conductivity, as a result of an increase or decrease in the number of electrons in the conduction band. Such an effect may be obtained by the application of an externally applied electric field to the semiconductor which supplies sufficient energy for a number of valence electrons to enter the conduction band and thus become available to conduct electricity through the material. The energy to promote an electron from the valence band to the conduction band is termed the Fermi energy level. This description explains the basis for the operation of a field effect transistor.

SUMMARY OF THE PRESENT INVENTION

The present invention makes use of this semiconductive phenomenon by utilizing the electrical characteristics of a specific binding substance, such as an antibody molecule, to influence the conductivity state of a semiconductor; thus by measuring the conductivity of said semiconductor, one can determine the binding of an analyte by its specific binding substance as a result of the change in its electrical characteristics and the resultant change in its influence on the semiconductor.

The preferred embodiment utilizes a semiconductive organic polymer, known as polyacetylene. Polyacetylene, having the general chemical formula $(CH)_x$, displays semiconductive properties in part as a result of extensive, alternating conjugated pi bonding orbitals of the carbon-carbon bonds. In conjunction with a specific binding substance, the semiconductive properties can be altered in a measureable fashion to effect the principle of the present invention.

The term "analyte" as used herein refers to antigens, antibodies, haptens, enzymes and enzyme substrates. The term "specific binding substance" is any substance or group of substances having a specific binding affinity for the analyte to the exclusion of other substances.

DESCRIPTION OF SPECIFIC EMBODIMENTS

Figure 1:
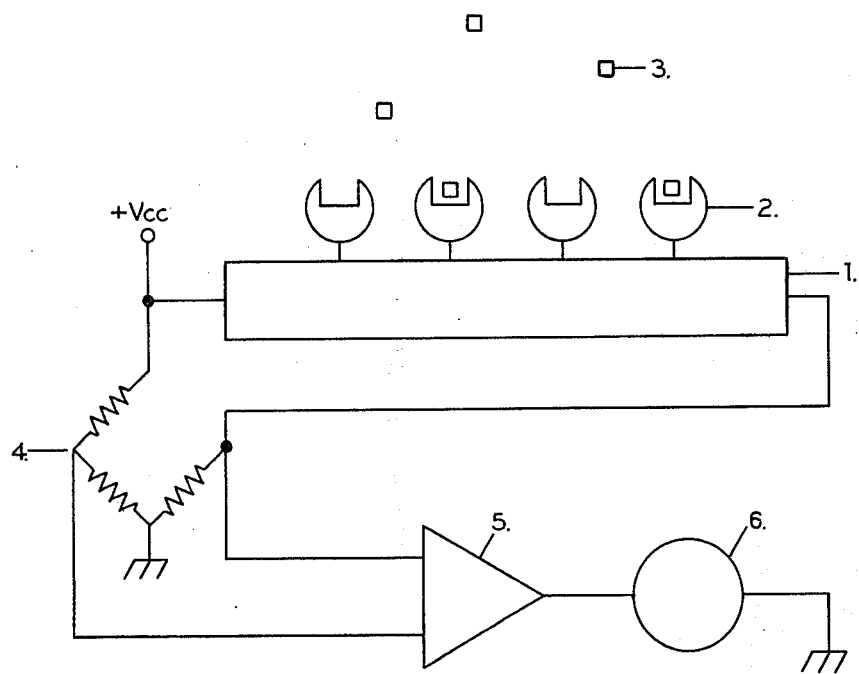
FIG. 1 is a schematic showing the semiconductive sensor in its electrical measurement circuit.
Figure 2:
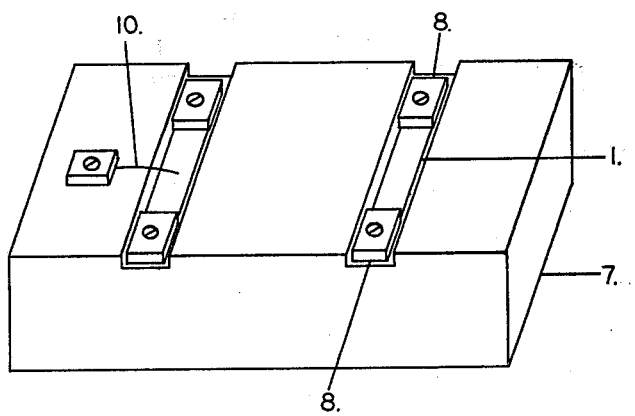
FIG. 2 is a representation of the semiconductive sensor.

The following specific description is given to enable those skilled in the art to more clearly understand and practice the present invention. It should not be considered as a limitation upon the scope of the invention but merely as being illustrative and representative thereof.

Preparation A

The IgG fraction of goat anti-rabbit IgG serum was isolated by a combination of 33% ammonium sulfate precipitation and DEAE cellulose chromatography as described by Garvey, J. S. et al. (1970) in *Methods in Immunology*, pp. 193-198, W. A. Benjamin Inc. Further specific purification, as necessary, was effected by the technique of affinity chromatography, various procedures of which are described in the literature.

Preparation B

The trans-polymer of acetylene was prepared, using a Zeigler-type catalyst, following the procedure of Ito et al., Journal of Polymer Science, 12,11, (1974).

EXAMPLE I

Strips of freshly synthesized polyacetylene, approximately 4×20 mm, were placed in a 0.05 M carbonate-bicarbonate buffer, pH 9.5 containing 5 mg/ml of purified goat anti-rabbit IgG and incubated overnight at room temperature. The polyacetylene-antibody strips were subsequently washed with a saline solution and stored under nitrogen.

The polyacetylene-antibody strips (1) were mounted on a teflon block (7) using two conductive gold clamps (8) to secure the strip in place and provide for two electrical connections spaced 5 mm apart. This resulting two port device was connected to a Wheatstone bridge (4) which was connected to a variable voltage, direct current, power supply. The voltage difference in the Wheatstone bridge network was amplified by a differential amplifier (5) which was connected to a suitable voltmeter (6), as the first step voltage is applied to the Wheatstone bridge and that network adjusted to provide a suitable "null" reading on the voltmeter. Then, 10 μl of a suitable dilution of a purified IgG fraction of rabbit serum is placed on the antibody-polyacetylene strip while recording the reading on the voltmeter as a function of time. The amplified change in voltage with time reflected the kinetic aspects of the antigen-antibody binding reaction. When the voltmeter reading stabilized (after 3 to 10 minutes), the Wheatstone bridge circuit was readjusted to the initial null reading with a suitably calibrated potentiometer.

Variations on the above procedure were made in order to obtain the desired results and to rule out effects resulting from other variables not related specifically to the antigen-antibody binding reaction. Those variations include differences in applied voltage, degree of amplification, and the extent of dilution required for the rabbit IgG solution. To further rule out non-specific effects, two polyacetylene-antibody devices were connected in the Wheatstone bridge circuit and electrically balanced. The experiment was repeated with one device receiving the diluent (saline), not containing the rabbit IgG. From this example, various concentrations of rabbit IgG produced predictable changes in the conductivity of the polyacetylene-antibody film.

EXAMPLE II

As in Example I, a strip of polyacetylene-antibody was prepared, using a goat anti-rabbit IgG preparation, and placed in a teflon holder. A mesh with a 3 mm diameter cutout was placed over the polyacetylene film and used to overlay an aqueous gelatin film, taking the precaution not to physically or electrically connect the two conductive clamps with the gelatin film. A measurement of the specific analyte was made with this device as described in Example I.

EXAMPLE III

As in Example II, a strip of polyacetylene-antibody-gelatin film was prepared except that a third electrical connection was formed by placing a piece of platinum wire (10) just on the surface of the gelatin film. In this example, the device is similar in principle to a field effect transistor. This third electrical connection allows for the application of an electrical potential at a right angle to the flow of electrons through the polyacetylene-antibody film. Using this device, the binding of rabbit IgG to goat anti-rabbit IgG antibody was ascertained as described in Examples I and II.

The invention being thus described, it will be obvious that the same may be varied in many ways. Such variations are not to be regarded as a departure from the spirit and scope of the invention, and all such modifications are to be included within the scope of the following claims.

Having thus set forth the nature of the invention, what is claimed is:

1. A device for determining the concentration of an analyte in a medium, comprising:
    (a) sensor means including an element whose resistance varies in response to the presence of an analyte, where said element includes a binding substance which has specific affinity for the analyte,
    (b) means including spaced-apart electrodes contacting the element for measuring the resistance of the element,
    (c) means for bringing the medium in contact with the sensor, wherein the improvement comprises: said element being constructed of polyacetylene.

2. The device as in claim 1 where there are two electrodes.

3. The device as in claim 1 where there are three electrodes.

4. A device as in claim 1, 2 or 3 where the specific binding substance is selected from the group consisting of an antibody, an antigen, an enzyme, an enzyme substrate, an enzyme substrate analog, an agglutinin or lectin, an enzyme cofactor, an enzyme inhibitor and a hormone.

5. A variable resistance sensor for determination of an analyte in a medium comprising: an insulating structure, element means having an active part composed of polyacetylene mounted on said structure for exposure to the medium and electrodes positioned to contact the element, and where the polyacetylene element means includes a specific binding substance for the analyte.

6. The sensor as in claim 5 where there are two electrodes.

7. The sensor as in claim 5 where there are three electrodes.

8. The sensor as in claim 5, 6 or 7, where the specific binding substance is selected from the group consisting of antibodies, antigens, enzymes, enzyme substrates, analoges of enzyme substrates, agglutinins, lectins, enzyme cofactors, enzyme inhibitors and hormones.

9. A method of identifying the type and quantity of an analyte in a medium comprising the steps of:
  (a) preparing an element of polyacetylene
  (b) treating the element with a specific binding substance,
  (c) exposing the element to the medium,
  (d) measuring the change in an electrical characteristic of the treated element.

10. The method of claim 9 including the steps of applying at least two electrodes to contact the element and measuring the electrical changes between the electrodes.

11. The method of claim 10 including the step of applying three electrodes to contact the element.

12. The method as in claim 9, 10 or 11, where the specific binding substance is selected from the group consisting of an antibody, an antigen, an enzyme, an enzyme substrate, an enzyme substrate analog, an agglutinin or lectin, an enzyme cofactor, an enzyme inhibitor and a hormone.

* * * * *